(12) United States Patent
Engel et al.

(10) Patent No.: US 6,422,237 B1
(45) Date of Patent: Jul. 23, 2002

(54) RESPIRATOR WITH A BREATHING CIRCUIT

(75) Inventors: Dieter Engel, Reinfeld; Jürgen Manigel, Klingberg; Claus Bunke, Sereetz; Matthias Witt, Lübeck, all of (DE)

(73) Assignee: Dräger Medizintechnik GmbH (DE)

( * ) Notice: Subject to any disclaimer, the term of this patent is extended or adjusted under 35 U.S.C. 154(b) by 0 days.

(21) Appl. No.: 09/472,566

(22) Filed: Dec. 27, 1999

(30) Foreign Application Priority Data

May 18, 1999 (DE) .......................................... 199 22 717

(51) Int. Cl.$^7$ ............................................ A61M 16/00
(52) U.S. Cl. ............................ 128/204.21; 128/204.18
(58) Field of Search ....................... 128/200.24, 203.12, 128/203.13, 203.14, 203.25, 204.18, 204.21, 204.23, 204.24, 204.28, 205.13, 205.14, 205.17, 205.28, 207.14, 207.16, 205.11

(56) References Cited

U.S. PATENT DOCUMENTS

| | | | | |
|---|---|---|---|---|
| 4,637,386 A | * | 1/1987 | Baum ..................... | 128/204.21 |
| 4,957,107 A | * | 9/1990 | Sipin ..................... | 128/204.21 |
| 5,868,133 A | * | 2/1999 | DeVries et al. ......... | 128/204.18 |
| 5,881,722 A | * | 3/1999 | DeVries et al. ......... | 128/204.21 |
| 6,041,777 A | * | 3/2000 | Faithfull et al. ........ | 128/200.24 |
| 6,131,571 A | * | 10/2000 | Lampotang et al. ... | 128/204.21 |
| 6,142,150 A | * | 11/2000 | O'Mahoney ........... | 128/205.18 |
| 6,152,131 A | * | 11/2000 | Heinonen ............... | 128/204.23 |
| 6,152,135 A | * | 11/2000 | DeVries et al. ......... | 128/204.18 |
| 6,186,143 B1 | * | 2/2001 | Baum ..................... | 128/205.11 |
| 6,196,222 B1 | * | 3/2001 | Heinonen et al. ...... | 128/204.23 |
| 6,213,119 B1 | * | 4/2001 | Brydon et al. .......... | 128/204.23 |

FOREIGN PATENT DOCUMENTS

DE           34 22 066 C2      12/1985

* cited by examiner

Primary Examiner—John G. Weiss
Assistant Examiner—Teena Mitchell
(74) Attorney, Agent, or Firm—McGlew and Tuttle, P.C.

(57) ABSTRACT

An improved respirator with a breathing circuit (100) and a corresponding process for operating the respirator are provided. Defined breathing gas volumes can be delivered to the patient and the current operating state can be reliably monitored despite a strong breathing gas volume flow being delivered in the breathing circuit (100). A gas delivery element (1) designed as a rotary compressor is connected on the inlet side to a reversible breathing gas reservoir (7) and on the outlet side to a patient connection piece (9) for inspiration via a first gas volume flow sensor (2) with a first nonreturn valve (11). A second gas volume flow sensor (5) is located in the connection line between the patient connection piece (9) and the patient being inspirated. The patient connection piece (9) is connected for expiration to a second nonreturn valve (10) via a third gas volume flow sensor (3) and to the reversible breathing gas reservoir (7) via a controllable shut-off valve (4). At least one measuring and control device (14, 15) is connected to the gas volume flow sensors (2, 5, 3), it receives their measured signals and sends control signals to the gas delivery element (1) and to the controllable shut-off valve (4).

14 Claims, 2 Drawing Sheets

RESPIRATOR WITH A BREATHING CIRCUIT

FIELD OF THE INVENTION

The present invention pertains to a respirator with a breathing circuit between the gas delivery element and the patient connection piece and a process for operating a respirator.

BACKGROUND OF THE INVENTION

Respirators with a breathing circuit are used either in the area of intensive respiration performed over long periods of time or as anesthesia apparatuses with corresponding metering means for metering anesthetics into the breathing circuit in order to guarantee a possibly controlled release to the patient being respirated, e.g., before and during an operation.

A respirator with a breathing circuit with a gas delivery element is described in DE 34 22 066 C2. However, there is no possibility with the disclosed system to ensure a defined gas volume flow to the patient during the phases of inspiration and to make possible the monitoring of the current operating state.

SUMMARY AND OBJECTS OF THE INVENTION

The primary object of the present invention is to provide a respirator with a breathing circuit and a corresponding process for operating the respirator, with which defined breathing gas volumes are delivered to the patient despite a strong breathing gas volume flow guided in the breathing circuit and the current operating state can be reliably monitored.

According to the invention, a respirator with a breathing circuit is provided with a gas delivery element designed as a rotary compressor connected on an inlet side to a reversible breathing gas reservoir and on the outlet side to a patient connection piece for inspiration via a first gas volume flow sensor with a first nonreturn valve. A second gas volume flow sensor is located in the connection line between the patient connection piece and the patient being respirated. A patient connection is connected for expiration to a second nonreturn valve via a third gas volume flow sensor and to a reversible breathing gas reservoir via a controllable shut-off valve. At least one measuring and control unit is connected to the gas volume flow sensors. The control unit receives their measured signals and sends control signals to the gas delivery element and to the controllable shut-off valve.

According to another aspect of the invention, a process for operating a respirator is provided wherein the beginning of each phase of inspiration and/or expiration is triggered either in a time-controlled manner or by a measured signal brought about by inspiration or expiration at the second gas volume flow sensor. In one mode of operation during each phase of inspiration, the controllable shut-off valve is closed, the gas delivery element is activated, so that it delivers breathing gas from the reversible breathing gas reservoir, and the speed of rotation of the gas delivery element is controlled as a function of the measured signals of the first gas volume flow sensor. During each phase of expiration, the speed of rotation of the gas delivery element is reduced to a lower value or to zero, the controllable shut-off valve is opened, and the exhaled gas volume flow is measured by means of a second gas volume flow sensor, and the speed of rotation of the gas delivery element is controlled as a function of the measured signals of the first gas volume flow sensor. During the switching phases of the controllable shut-off valve, the gas volume flow to the patient is determined from the difference of the measured signals of the first and third gas volume flow sensors at the beginning and at the end of each phase of inspiration, and the speed of rotation of the gas delivery element is controlled as a function of this difference.

One essential advantage of the present invention is the use of a gas delivery element, which is designed as a rotary compressor, especially a radial compressor, which can have a highly compact design and can be controlled very rapidly due to its dynamic properties by setting the speed of rotation. To obtain the most homogeneous breathing gas concentration possible in the breathing circuit, the breathing gas is circulated through the gas delivery element with a high speed of rotation and high delivery capacity before each phase of inspiration, i.e., a so-called rinsing gas volume flow of a time average of, e.g., 30 L per minute is generated.

During each phase of inspiration, according to one mode of operation, the expiratory branch of the breathing circuit is completely closed by means of a controllable shut-off valve, so that no expiratory gas volume flow is present in the expiratory branch and no rinsing gas volume flow guided in the breathing circuit is present. The inspiratory gas volume flow in the inspiratory branch of the breathing circuit is measured by means of a first gas volume flow sensor and it directly corresponds to the gas volume flow to the patient. The respirator is controlled by means of one central measuring and control unit or a plurality of measuring and control units as a function of this measured gas volume flow to the patient, so that a defined patient volume can be metered in a time-dependent manner. The gas volume flow measurement is performed during this phase only via the first gas volume flow sensor, so that the accuracy of the measurement depends directly on the accuracy of the first gas volume flow sensor itself.

The expiratory branch of the breathing circuit is opened by means of the controllable shut-off valve during each phase of expiration after the speed of rotation of the gas delivery element has first been reduced to a lower value or even to zero and the patient is breathing out.

In addition to the gas volume flow exhaled by the patient, a rinsing gas volume flow is metered by means of the gas delivery element by increasing the speed of rotation of the gas delivery element, the amount of the rinsing gas volume flow being such that extensive homogenization of the breathing gas concentration is achieved in the breathing circuit, on the average, in the course of one breath. Since the exhaled gas volume flow and the rinsing gas volume flow are superimposed to one another in the expiratory branch of the breathing circuit, the exhaled gas volume flow is determined directly by means of a second gas volume flow sensor in the connection line between the patient connection piece and the patient being respirated. Finally, the inspiratory gas volume flow to the patient, in one mode of operation, is determined during the switching phases of the controllable shut-off valve at the beginning and at the end of each phase of inspiration from the difference of the measured signals of the first and third gas volume flow sensors arranged in the inspiratory branch and in the expiratory branch of the breathing circuit, because the difference of these measured signals is also relatively small at high rinsing gas volume flows and is subject to high inaccuracies. The speed of rotation of the gas delivery element is controlled during these switching phases as a function of this difference of the measured signals.

Another mode of operation of the respirator includes triggering the beginning of each phase of inspiration and/or expiration either in a time-controlled manner or by a measured signal brought about by inspiration or expiration at the second gas volume flow sensor. The controllable shut-off valve is controlled during each phase of inspiration with the third gas volume flow sensor such that a gas volume flow is maintained in the respirator and the speed of rotation of the gas delivery element is only controlled as a function of the pressure detected in the respirator. The speed of rotation of the gas delivery element is reduced during each phase of expiration to a lower value or to zero. The controllable shut-off valve is opened, and the exhaled gas volume flow is measured with the second gas volume flow sensor. The speed of rotation of the gas delivery element is controlled during expiration as a function of measured signals of the first gas volume flow sensor.

The further process feature of switching between the first mode and the second mode provides advantages including a more versatile system.

One exemplary embodiment of the present invention will be explained in greater detail below on the basis of the only figure, which schematically shows the arrangement of a respirator according to the present invention, adapted to the requirements in the area of anesthesia.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
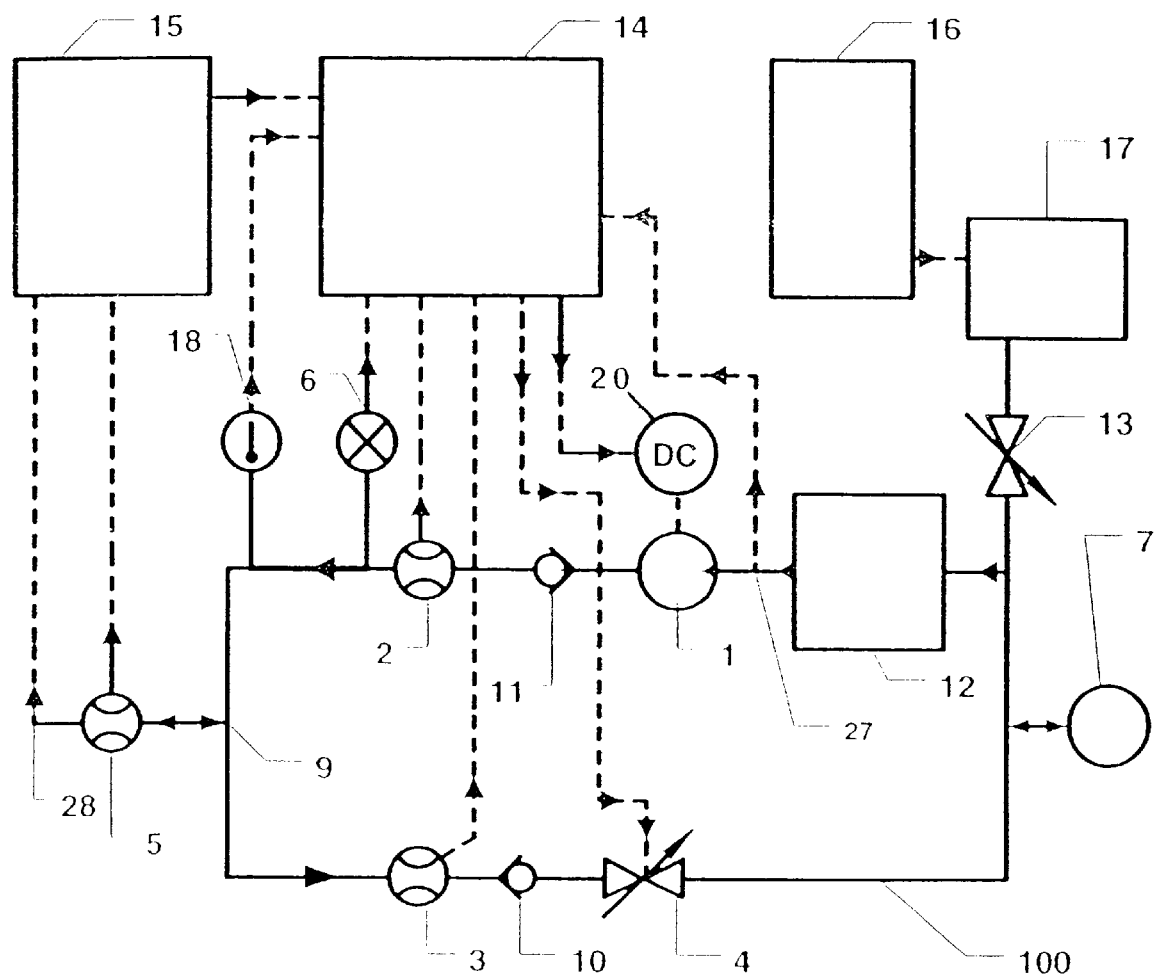
FIG. 1 is a schematic view of the respirator and breathing circuit including a d.c. motor drive for the radial compressor.

Referring to the drawings in particular, the breathing circuit 100 shown has, first of all, a rotary compressor and, in particular, a gas delivery element 1 designed as a radial compressor, which is able to rapidly respond to corresponding control signals due to its compact design and dynamic properties and to generate a continuous rinsing gas volume flow of up to 30 L per minute as the time average of one breath in the breathing circuit 100.

The breathing circuit 100 may be operated either by means of a central measuring and control unit 14, which also integrates the functions of the gas control unit 16 and/or the evaluating and monitoring unit 15 in this case, or, as is shown, by means of a plurality of separate or combined measuring and regulating or control units.

Figure 2:
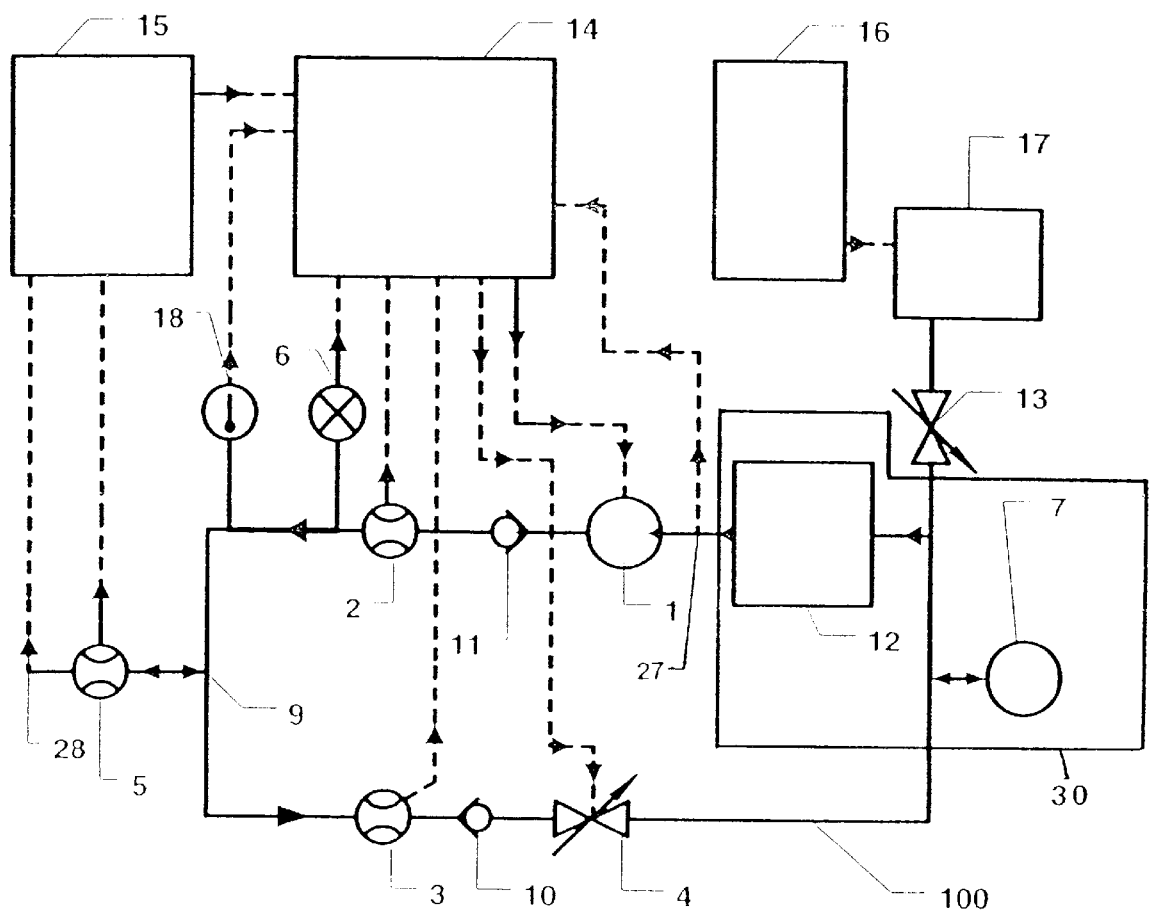
FIG. 2 is a schematic view of the respirator and breathing circuit including a reversible breathing gas reservoir and $CO_2$ absorber as an integral component.

The following features are decisive for the function of the present invention in the case of use for anesthesia:

The gas delivery element 1 designed as a rotary compressor and especially as a radial compressor driven by a d.c. motor 20 (FIG. 1) is connected on the inlet side to a fresh gas reservoir 17 and to a reversible breathing gas reservoir 7, e.g., a breathing gas bag, via a $CO_2$ absorber 12 and a fresh gas and anesthesia gas metering unit 13. The reversible breathing gas reservoir 7 and the $CO_2$ absorber 12 may be in the form of an integral component 30 as shown in FIG. 2.

On the outlet side, i.e., the pressure side or outlet branch, the gas delivery element 1 is connected via a first gas volume flow sensor 2 with a respective first nonreturn valve 11 with a patient connection piece 9, especially a Y piece. The first nonreturn valve 11 can either be located upstream of the first gas volume flow sensor 2, as shown, or alternatively downstream of it. A second gas volume flow sensor 5 is arranged in the connection line between the patient connection piece 9 and the patient P. The second gas volume flow sensor 5 is designed especially as a hot wire anemometer and is able to detect even small gas volume flows of, e.g., a few L per minute, from and to the patient with high accuracy, so that corresponding trigger signals for activating and deactivating the gas delivery element 1 are generated. The evaluating and monitoring unit 15 receives gas samples from the connection line leading to the patient P from a suction point 28 located close to the patient in order to compensate and to take into account the gas type dependence of the measured signals of the gas volume flow sensor 5 after measurement by means of suitable algorithms.

The measured signal of the first gas volume flow sensor 2 is likewise compensated by calculation in the measuring and control unit 14 in terms of the pressure and temperature effects. To do so, the temperature and the pressure in the breathing circuit are transmitted to the measuring and control unit 14 by means of suitable measuring transducers for the temperature 18 and for the pressure 6 in the form of electric signals and are taken into account there.

Gas samples are taken at an additional suction site 27 in the inspiratory (outlet) branch of the breathing circuit 100 for the gas type-dependent measurement evaluation of the first and third gas volume flow sensors 2 and 3 in order to compensate the gas type dependence of the measured signals of the first and third gas volume flow sensors 2 and 3 after suitable measurement, e.g., by light absorption measurement, and by means of suitable algorithms.

A second nonreturn valve 10, which lets gas through in the case of expiration only, with the shut-off valve 4 open, is located between the third gas volume flow sensor 3 and the controllable shut-off valve 4. The controllable shut-off valve 4 is preferably a solenoid valve that can be rapidly switched electrically.

Based on the signals measured in the breathing circuit 100 and the time and respiration patterns programmed and/or stored in the measuring and control unit 14, the breathing gas transport in the breathing circuit 100 is controlled by the measuring and control unit 14 by means of the gas delivery element 1 and the controllable shut-off valve 4, which act as adjusting members.

The process according to the present invention includes operation of the respirator in either one of two modes. The respirator may be operated exclusively in either one of these modes or with a switching means, such as an input to the central measuring and control unit 14, and/or the evaluating and monitoring unit 15 or by means of a plurality of separate or combined measuring and regulating or control units.

The first mode of operation of the respirator includes the following process steps:

The beginning of each inspiration and/or expiration phase is triggered either in a time-controlled manner or by a measured signal at the second gas volume flow sensor 5, which measured signal is brought about by the inspiration or the expiration;

the controllable shut-off valve 4 is closed during each phase of inspiration, and the gas delivery element 1 is activated, so that it delivers breathing gas from the reversible breathing gas reservoir 7, and the speed of rotation of the gas delivery element 1 is controlled as a function of the measured signals of the first gas volume flow sensor 2;

during each phase of expiration, the speed of rotation of the gas delivery element 1 is reduced to a lower value or even to zero and the controllable shut-off valve 4 is opened, and the exhaled gas volume flow is measured by means of the second gas volume flow sensor 5 and the speed of rotation of the gas delivery element 1 is controlled as a function of the measured signals of the first gas volume flow sensor 2;

the gas volume flow to the patient is determined from the difference of the measured signals of the first and third gas volume flow sensors 2, 3 during the switching phases of the controllable shut-off valve 4 at the beginning and at the end of each phase of inspiration, and the speed of rotation of the gas delivery element 1 is controlled as a function of this difference.

The second mode of operation of the respirator includes the following process steps:

triggering the beginning of each phase of inspiration and/or expiration either in a time-controlled manner or by a measured signal brought about by inspiration or expiration at the second gas volume flow sensor;

during each phase of inspiration,
controlling the controllable shut-off valve with the third gas volume flow sensor such that a gas volume flow is maintained in the respirator and
controlling the speed of rotation of the gas delivery element only as a function of the pressure detected in the respirator (that is based on the signal from pressure sensor 6 connected to the inspiratory branch and/or based on another pressure sensor signal from a pressure sensor connected to the expiratory branch), the sensed values are compared with a target pressure value which has been selected and set by the operator/physician to obtain the desired pressure for the patient; and during each phase of expiration
reducing a speed of rotation of the gas delivery element to a lower value or to zero,
opening the controllable shut-off valve, and
measuring the exhaled gas volume flow with the second gas volume flow sensor, and controlling the speed of rotation of the gas delivery element as a function of measured signals of the first gas volume flow sensor.

The further process feature of switching between the first mode and the second mode provides advantages including a more versatile system.

While a specific embodiment of the invention has been shown and described in detail to illustrate the application of the principles of the invention, it will be understood that the invention may be embodied otherwise without departing from such principles.

What is claimed is:

1. A respirator comprising:
a breathing circuit with an inlet branch and an outlet branch;
a reversible breathing gas reservoir;
a first gas volume flow sensor;
a patient connection piece;
a first nonreturn valve;
a gas delivery element including a rotary compressor, said gas delivery element being connected on an inlet branch to said reversible breathing gas reservoir and being connected on an outlet branch to said patient connection piece for inspiration via said first gas volume flow sensor with said first nonreturn valve;
a second nonreturn valve;
a controllable shut-off valve connected to said outlet branch providing an open state allowing flow through said outlet branch and a shut state stopping flow through said outlet branch;
a connection line between said patient connection piece and a patient being respirated;
a second gas volume flow sensor located in said connection line between said patient connection piece and the patient being respirated;
a third gas volume flow sensor; said patient connection piece being connected for expiration to said second nonreturn valve via said third gas volume flow sensor and to said reversible breathing gas reservoir via said controllable shut-off valve; and
a measuring and control unit connected to said gas volume flow sensors receiving measured signals and sending control signals to said gas delivery element to control a speed of said gas delivery element and to said controllable shut-off valve to control the open and shut state of said controllable shut-off valve.

2. The respirator in accordance with claim 1, further comprising:
a fresh gas and anesthesia gas metering device with a fresh gas reservoir and a $CO_2$ absorber arranged between said gas delivery element and said reversible breathing gas reservoir.

3. The respirator in accordance with claim 1, further comprising:
measuring transducers for measuring temperature and/or pressure, said measuring transducers being arranged in said outlet branch of said breathing circuit between said gas delivery element and said patient connection piece, said measuring transducers being connected to said measuring and control unit with said measuring transducers generating measuring signals which are sent to said measuring and control unit.

4. The respirator in accordance with claim 1, further comprising an evaluating unit associated with said control unit and a suction site located close to said patient in said connection line between said patient connection piece and said patient to take gas samples, said gas samples being evaluated in said evaluating unit to determine the content of gas in said connection line between said patient connection piece and said patient.

5. The respirator in accordance with claim 4, further comprising an additional suction site provided in said outlet branch of said breathing circuit to take outlet branch gas samples, said outlet branch gas samples being evaluated in said evaluating unit to determine the content of gas in said outlet branch.

6. The respirator in accordance with claim 1, wherein said gas delivery element is a radial compressor, which is driven by means of a d.c. electric motor.

7. The respirator in accordance with claim 2, wherein said reversible breathing gas reservoir and said $CO_2$ absorber are an integral component.

8. A process for operating a respirator, the process comprising the steps of:
providing a breathing circuit with a patient connection piece and a connection line between said patient connection piece and a patient being respirated;

providing a reversible breathing gas reservoir;
providing a first gas volume flow sensor, a second gas volume flow sensor located in said connection line between said patient connection piece and said patient being respirated and a third gas volume flow sensor;
providing a first nonreturn valve, a second nonreturn valve and a controllable shut-off valve;
providing a gas delivery element including a rotary compressor;
connecting an intake of said gas delivery element to said reversible breathing gas reservoir and connecting a discharge of said gas delivery element to said patient connection piece, for inspiration via said first gas volume flow sensor and said first nonreturn valve;
connecting said patient connection piece for expiration to said second nonreturn valve via said third gas volume flow sensor and to said reversible breathing gas reservoir via said controllable shut-off valve;
receiving measurement signals from said gas volume flow sensors at a measuring and control device and sending control signals from said control device to said gas delivery element to control a speed of operation of said gas delivery element and sending control signals from said control device to said controllable shut-off valve to control the open and shut status of said controllable shut-off valve;
triggering the beginning of each phase of inspiration and/or expiration either in a time-controlled manner or by a measured signal brought about by inspiration or expiration by the patient detected at said second gas volume flow sensor;
closing said controllable shut-off valve during each phase of inspiration, with said gas delivery element activated, so that said gas delivery element delivers breathing gas from said reversible breathing gas reservoir;
controlling a speed of rotation of said gas delivery element during each phase of inspiration as a function of said measured signals of said first gas volume flow sensor;
reducing the speed of rotation of said gas delivery element during each phase of expiration to a lower value or to zero;
opening said controllable shut-off valve during each phase of expiration;
measuring an exhaled gas volume flow with said second gas volume flow sensor during each phase of expiration;
controlling the speed of rotation of said gas delivery element as a function of measured signals of said first gas volume flow sensor during each phase of expiration; and
determining a gas volume flow to said patient from a difference of said measured signals of said first and said third gas volume flow sensors during opening and closing of said controllable shut-off valve at a beginning and at an end of each phase of inspiration, and controlling the speed of rotation of said gas delivery element during inspiration as a function of this difference.

9. The process in accordance with claim 8, wherein the speed of rotation of said gas delivery element is controlled as a function of a pressure actually measured in said breathing circuit and said gas volume flow actually measured in said breathing circuit.

10. The process in accordance with claim 8, wherein a measured signal is sent to said measuring and control device by means of said second gas volume flow sensor at a beginning of said inspiration by the patient, so that said controllable shut-off valve is closed via said measuring and control device and said gas delivery element is activated by increasing the speed of rotation of said gas delivery element.

11. The process in accordance with claim 10, wherein at the end of the inspiration, said measuring and control device first reduces the speed of rotation of said gas delivery element and opens said controllable shut-off valve based on the measured signal received from said first gas volume flow sensor or from said second gas volume flow sensor.

12. A process for operating a respirator, the process comprising the steps of:
providing a breathing circuit with a patient connection piece and a connection line between said patient connection piece and a patient being respirated;
providing a reversible breathing gas reservoir;
providing a first gas volume flow sensor, a second gas volume flow sensor located in said connection line between said patient connection piece and a patient being respirated and a third gas volume flow sensor;
providing a first nonreturn valve, a second nonreturn valve and a controllable shut-off valve;
providing a gas delivery element including a rotary compressor;
connecting an intake of said gas delivery element to said reversible breathing gas reservoir and connecting a discharge of said gas delivery element to said patient connection piece for inspiration via said first gas volume flow sensor and said first nonreturn valve;
connecting said patient connection piece for expiration to said second nonreturn valve via said third gas volume flow sensor and to said reversible breathing gas reservoir via said controllable shut-off valve;
receiving measured signals from said gas volume flow sensors at a measuring and control device and sending control signals to said gas delivery element and to said controllable shut-off valve;
triggering the beginning of each phase of inspiration and/or expiration either in a time-controlled manner or by a measured signal brought about by patient inspiration or expiration detected at said second gas volume flow sensor;
during each phase of inspiration, controlling said controllable shut-off valve with said third gas volume flow sensor such that a gas volume flow is maintained in the respirator and controlling the speed of rotation of said gas delivery element as a function of the pressure detected in the respirator only; and
during each phase of expiration, reducing a speed of rotation of said gas delivery element to a lower value or to zero, opening said controllable shut-off valve, measuring exhaled gas volume flow with said second gas volume flow sensor, and controlling the speed of rotation of said gas delivery element as a function of measured signals of said first gas volume flow sensor.

13. A process for operating a respirator, the process comprising the steps of:
providing a breathing circuit with a patient connection piece and a connection line between said patient connection piece and a patient being respirated;
providing a reversible breathing gas reservoir;
providing a first gas volume flow sensor, a second gas volume flow sensor located in said connection line between said patient connection piece and said patient being respirated and a third gas volume flow sensor;

providing a first nonreturn valve, a second nonreturn valve and a controllable shut-off valve;

providing a gas delivery element including a rotary compressor;

connecting said gas delivery element, being on an inlet branch to said reversible breathing gas reservoir and on an outlet branch to said patient connection piece for inspiration via said first gas volume flow sensor with said first nonreturn valve;

connecting said patient connection piece for expiration to said second nonreturn valve via said third gas volume flow sensor and to said reversible breathing gas reservoir via said controllable shut-off valve;

receiving measured signals from said gas volume flow sensors at a measuring and control device and sending control signals to said gas delivery element and to said controllable shut-off valve;

triggering the beginning of each phase of inspiration and/or expiration either in a time-controlled manner or by a measured signal brought about by inspiration or expiration at said second gas volume flow sensor;

reducing a speed of rotation of said gas delivery element during each phase of expiration to a lower value or to zero, opening said controllable shut-off valve, and measuring said exhaled gas volume flow with said second gas volume flow sensor, and controlling the speed of rotation of said gas delivery element as a function of measured signals of said first gas volume flow sensor;

providing a first mode of operation including closing said controllable shut-off valve during each phase of inspiration, with said gas delivery element activated, so that said gas delivery element delivers breathing gas from said reversible breathing gas reservoir, and said speed of rotation of said gas delivery element is controlled as a function of said measured signals of said first gas volume flow sensor and determining a gas volume flow to said patient from a difference of said measured signals of said first and said third gas volume flow sensors during a switching phases of said controllable shut-off valve at a beginning and at an end of each phase of inspiration, and controlling a speed of rotation of said gas delivery element as a function of this difference; and providing a second mode of operation including controlling said controllable shut-off valve during each phase of inspiration with said third gas volume flow sensor such that a gas volume flow is maintained in the respirator and the speed of rotation of said gas delivery element is only controlled as a function of the pressure detected in the respirator during each phase of inspiration.

14. A process for operating a respirator in accordance with claim 13, further comprising the steps of:

providing a switching means associated with said respirator for switching between said first mode of operation and said second mode of operation; and switching between said first mode of operation and said second mode of operation.

* * * * *